(12) United States Patent
Gupta

(10) Patent No.: US 8,178,134 B2
(45) Date of Patent: May 15, 2012

(54) SYNERGISTIC HERBAL OPHTHALMIC FORMULATION FOR LOWERING INTRAOCULAR PRESSURE IN CASE OF GLAUCOMA

(75) Inventor: Suresh Kumar Gupta, New Delhi (IN)

(73) Assignee: Delhi Institute of Pharmaceuticals and Research, New Delhi (IN)

( * ) Notice: Subject to any disclaimer, the term of this patent is extended or adjusted under 35 U.S.C. 154(b) by 87 days.

(21) Appl. No.: 12/216,041

(22) Filed: Jun. 27, 2008

(65) Prior Publication Data
US 2009/0175972 A1    Jul. 9, 2009

(30) Foreign Application Priority Data
Jan. 3, 2008    (IN) ................. 29/DEL/2008

(51) Int. Cl.
*A01N 65/00*    (2009.01)
(52) U.S. Cl. ....................................... 424/725
(58) Field of Classification Search ............... None
See application file for complete search history.

(56) References Cited

U.S. PATENT DOCUMENTS

| | | | | |
|---|---|---|---|---|
| 4,923,693 | A * | 5/1990 | Michalos | 424/59 |
| 5,342,625 | A * | 8/1994 | Hauer et al. | 424/455 |
| 7,495,076 | B2 * | 2/2009 | Gu et al. | 530/350 |
| 2004/0225004 | A1 * | 11/2004 | Zeligs | 514/419 |
| 2007/0269526 | A1 * | 11/2007 | Bos et al. | 424/502 |

FOREIGN PATENT DOCUMENTS

| | | | |
|---|---|---|---|
| JP | 06298649 | * | 10/1994 |
| JP | 2006036651 | * | 2/2006 |
| SU | 1803110 | * | 3/1993 |
| WO | WO 03/080091 A1 | | 10/2003 |
| WO | WO 2008/104856 A2 | | 9/2008 |

OTHER PUBLICATIONS

Jain et al., "Effect of Curcumin on Protein Glycosylation, Lipid Peroxidation, and Oxygen Radical Generation in Human Red Blood Cells Exposed to High Glucose Levels", Free Radical Biology & Medicine, vol. 41, pp. 92-96, 2006.
Sharma et al., "Anti-Cataract Activity of Ocimum *Sanctum* on Experimental Cataract", Indian Journal of Pharmacology, vol. 30, No. 1, pp. 16-20, Feb. 1998.
Dharmananda et al., "Treatment of Glaucoma with Chinese Herbs", retrieved from internet: http://www.itmonline.org/arts/glaucoma.htm, on Chapter "Topical Treatment", Jan. 1997.
Aug. 29, 2008 International Search Report issued in International Application No. PCT/IB2008/000419.
Sep. 1, 2009 International Preliminary Examination Report and Written Opinion issued in International Application No. PCT/IB/2008/000419.
U.S. Appl. No. 12/529,015, filed Nov. 3, 2009 in the name of Gupta et al.

* cited by examiner

*Primary Examiner* — Michael Meller
(74) *Attorney, Agent, or Firm* — Oliff & Berridge, PLC

(57) ABSTRACT

The present invention relates to an herbal ophthalmic composition of *Withania somnifera* and *Areca catechu*, which reduces intra ocular pressure of eyes in a synergistic manner. A composition of *Withania somnifera* and *Areca catechu* acts synergistically with the other ingredients when formulated as a composition of the present invention.

6 Claims, No Drawings

SYNERGISTIC HERBAL OPHTHALMIC FORMULATION FOR LOWERING INTRAOCULAR PRESSURE IN CASE OF GLAUCOMA

FIELD OF THE INVENTION

The present invention relates to a synergistic herbal ophthalmic composition for lowering the intra ocular pressure in glaucoma and process for the preparation of the same in pharmaceutically acceptable dosage forms.

BACKGROUND OF THE INVENTION

Glaucoma is a disease characterized by high intraocular pressure (IOP) sufficient to cause either temporary or permanent impairment of vision. The rise in IOP might be due to increased rate of aqueous formation, decreased rate of out flow, or raised pressure in the draining episcleral veins. An obstruction to the circulation of the aqueous at the pupil or to its drainage through the angle of the anterior chamber causes glaucoma. The normal IOP of an individual ranges from 20-30 mm Hg and can rise up to 60 to 70 mm of Hg in glaucoma patients. Raised IOP of this magnitude can result in loss of vision by causing damage to retinal nerve fibers. Optic nerve axons of the eyeball become compressed at the optic disc due to elevated IOP. This compression probably blocks the axonal flow of cytoplasm from the neuronal cell bodies in the retina to the extended optic nerve fibers entering the brain. This results in lack of nutrition of fibers and ultimately causes death of the neurons. Compression of retinal artery may increase the neuronal damage due to reduction in retinal nutrition. Thus reduction of IOP is an effective means for curing Glaucoma.

Prompt and effective management of glaucoma is necessary to reduce the incidence of cases of bilateral blindness due to progressive glaucoma. Biological revolution in medicine has provided new avenues for therapeutic intervention. Newer and innovative treatment strategies are being considered for the control of raised intraocular pressure (IOP) by the use of synthetic and herbal drugs in glaucoma. Herbal drugs are preferred to the synthetic drugs as they are economic, non toxic and safe. Moreover, in a sensitive organ like eye, a safer herbal formulation is preferred to a synthetic formulation.

There are some synthetic drugs used in the treatment of glaucoma like Latanoprost, Timolol, Brimonidine, Travoprost, Bimaprost, Pilocarpine etc. which can decrease aqueous production in the ciliary body or increase aqueous humor outflow through the trabecular meshwork or uveoscleral pathway but on long term use these agents cause side effects like bradycardia, tachyphylaxis, blurred vision, pigmentation etc, apart from their high cost of therapy. Some plants have been reported in the ancient literature for ophthalmic use but there are no scientific data on them. No herbal formulation is available for the treatment of glaucoma in the market. Hence an objective of the present invention is to provide a herbal formulation effective for the treatment of glaucoma.

OBJECTIVES OF THE INVENTION

The object of the present invention is to develop herbal synergistic composition for its study as IOP lowering and anti glaucoma potential in experimental models.

Another object of the present invention is to formulate the synergistic herbal composition in to pharmaceutically acceptable ophthalmic dosage form with optimum anti glaucoma activity.

SUMMARY OF THE INVENTION

The present invention relates to a synergistic ophthalmic composition prepared from *Withania Somnifera* in combination *Areca catechu* with HPMC for lowering IOP in glaucoma.

DETAILED DESCRIPTION OF THE INVENTION

Accordingly present invention provides a synergistic herbal ophthalmic formulation for lowering IOP in glaucoma.

The synergistic herbal composition of the present invention comprises extract of herbs selected from *Withania somnifera* and *Areca catechu* optionally along with a pharmaceutically acceptable excipient wherein the amount of *Withania somnifera* extract is in the range of 0.01% to 5.0%, *Areca catechu* extract is in the range of 0.01 to 5.0%. The excipients comprise, viscoelastic agent, solubility enhancing agent, antioxidant, preservative, osmolality agent, buffering agent.

Preferably, the amount of *Withania somnifera* extract in the composition is 1%, the preferred amount of *Areca catechu* extract is 0.50%.

The synergistic herbal composition of the present invention comprises as excipient a viscoelastic agent that is preferably selected from the group of carboxyl methyl cellulose, poly vinyl alcohol, hydroxy propyl methyl cellulose (HPMC), hydroxy ethyl cellulose, and other suitable cellulose derivative, poly vinyl alcohol, povidone, carbopol, caragenin and dextran. In general, the amount of the viscoelastic agent, i.e. such as HPMC contained in the composition is preferably 0.25 to 2% and most preferably 0.25%.

The composition also includes solubility enhancing agent such as polysorbate, cyclodextrin and their derivative, most preferably Cremophore RH40.

The composition may also include ananti oxidant such as citric acid, EDTA and salts thereof, sodium metabisulphite and other approved water soluble anti oxidant. The composition may further comprise a buffering agent such as citrate, borate, phosphate, citro phosphate and osmolarity adjusting agent such as sodium chloride, mannitol and glycerol.

The composition in addition may comprise a preservative such as benzalkonium chloride, sorbic acid, methyl paraben, propyl paraben, and salts thereof and most preferably Benzalkonium chloride, methyl paraben sodium, propyl paraben sodium and sorbic acid.

The composition of the present invention is preferably packaged in opaque plastic container, one that may be presented in the form of eye drops packed in glass vial preferably amber colored, BFS plastic vial desirably opaque or three-piece plastic vial most preferably in opaque plastic three piece vials. The composition may be formulated as drops, ointment, gel and cream most preferably as eye drops The viscosity of the composition may be 10-100 cps and most preferably 12.5 cps. The osmolality of the composition may be 250-450 and most preferably 250-300. The pH of the composition of the present invention may be between 4-8 and most preferably 5-7.

The composition may be clear, transparent having light brown color.

In yet another embodiment of the present invention, the composition of the present invention may be prepared by a process comprising.

1. obtaining a dry extract of *Withania somnifera* and *Areca catechu*
2. mixing the dry extract with a viscoelastic agent and solubility enhancing agent in water to obtain a solution
3. optionally purifying the solution of step (ii) to obtain a clear filtrate and adding a preservative and an antioxidant,
4. adjusting the pH of the solution of step (iii) to 5-7 and making up the desired volume with water for injection to obtain the composition.

ADVANTAGES

Composition of the type as illustrated by the present invention has been found to be substantially stable and efficacious to the composition without the viscoelastic agent and also in comparison to the compositions of the individual herbs.

The invention is described in detail herein below with respect to the following examples, which are provided merely for illustration and are not intended to restrict scope of invention in any manner. Any embodiments that may be apparent to a person skilled in the art are deemed to fall within the scope of present invention.

EXAMPLE 1

Preparation of Composition (i) *Withania somnifera* and *Areca catechu* with HPMC Ophthalmic Formulation (F4) of the Present Invention Comprises

| S.N. | Ingredients | Quantity for 100 ml (mg) |
|---|---|---|
| 1 | *Withania somnifera* extract | 1000 |
| 2 | *Areca catechu* extract | 500 |
| 3 | Hydroxy propyl methyl cellulose | 250 |
| 4 | Methyl paraben sodium | 200 |
| 5 | Propyl paraben sodium | 20 |
| 6 | Disodium EDTA | 100 |
| 7 | Sodium metabisulphite | 100 |
| 8 | Boric acid quantity sufficient to pH 6.5 | q.s. |
| 9 | Water for injection q.s.to volume | q.s. |

Procedure:

Hydroxy propyl methyl cellulose (HPMC) was dissolved in about 50 ml of water under stirring. Once it dissolved completely, the *Withania Somnifera* and *Areca catechu* extract were added to this and dissolved under stirring. The solution was then centrifuged at 5000 rpm for 30 minutes and clear liquid was collected. Methyl and propyl paraben was dissolved in around 10 ml of water and added to clear filtrate containing the extract and HPMC under stirring. To this solution disodium EDTA and sodium metabisulfite were then dissolved in main bulk under stirring. pH was then adjusted with dilute boric acid solution and volume is made up to desired level. The solution was filtered using 0.22 micron filtered aseptically and product was filled in 10 ml three piece plastic vials.

EXAMPLE 2

Effect of Composition on Antiglaucoma Activity in Normotensive Model for Glaucoma The composition of Example 1 was prepared (F4). Compositions similar to that of Example 1 was prepared but without certain ingredients in order to assess the synergistic effect of composition of example 1. A composition was prepared with the extract of *Withania somnifera* and HPMC but without the extract of *Areca catechu* (F1), another with the extract of *Areca catechu* and HPMC but without the extract of *Withania somifera* (F2). Further another composition comprising the extract of *Withania somnifera* and *Areca catechu* but without HPMC was prepared (F3).

The effect of composition as prepared in example 1 (F4) was compared with the other compositions, namely F1, F2 and F3. The anti glaucoma activity was evaluated by examining the IOP in rabbits using the normotensive model of glaucoma.

Twelve Albino rabbits of either sex weighing 1.5-2 kg were subjected for baseline IOP measurements using Non Contact Tonometer. The drug (50 μl) was then instilled into one of the eye while the other eye served as the control eye and was instilled with normal saline (50 μl). IOP was then recorded at different time intervals of 0,1,2,3,4,5, and 6 hours.

TABLE 1

IOP lowering effect of *Withania somnifera* with HPMC (F1) in normotensive model

| Time | % Change in IOP (from the baseline values) | | % Difference Treated |
|---|---|---|---|
| (hrs) | TE | CE | Eye − Control Eye |
| 0 | 0.00 | 0.00 | 0 |
| 0.5 | −12.14 | 0.34 | −12.48 |
| 1 | −14.69 | −2.08 | −12.61 |
| 1.5 | −17.37 | −2.95 | −14.42 |
| 2 | −19.19 | −1.72 | −17.47 |
| 2.5 | −23.10 | −3.02 | −20.08 |
| 3 | −18.90 | −3.36 | −15.54 |
| 3.5 | −15.28 | −3.36 | −11.92 |
| 4 | −13.79 | −1.32 | −12.47 |
| 5 | −7.22 | 0.90 | −8.12 |
| 6 | −3.24 | −0.39 | −2.85 |

TABLE 2

IOP lowering effect of *Areca catechu* with HPMC (F2) in normotensive model

| Time in hours | % Change in IOP Treated eye | % Change in IOP Control eye | % Difference in IOP Treated Eye − Control Eye |
|---|---|---|---|
| 0 | 0.00 | 0.00 | 0.00 |
| 0.5 | −13.59 | −2.54 | −11.05 |
| 1 | −17.63 | −1.16 | −16.47 |
| 1.5 | −19.68 | −1.94 | −17.74 |
| 2 | −20.60 | −0.75 | −19.85 |
| 3 | −17.53 | −2.58 | −14.95 |
| 4 | −15.71 | −1.23 | −14.48 |
| 5 | −9.88 | −0.48 | −9.41 |
| 6 | −5.54 | −2.96 | −2.58 |

TABLE 3

IOP lowering effect of *Withania somnifera* and *Areca catechu* without HPMC (F3) in normotensive model

| Time in hours | % Change in IOP Treated eye | % Change in IOP Control eye | % Difference in IOP Treated Eye − Control Eye |
|---|---|---|---|
| 0 | 0 | 0 | 0 |
| 1 | −13.61 | −1.31 | −12.30 |

TABLE 3-continued

IOP lowering effect of *Withania somnifera* and *Areca catechu* without HPMC (F3) in normotensive model

| Time in hours | % Change in IOP Treated eye | % Change in IOP Control eye | % Difference in IOP Treated Eye – Control Eye |
|---|---|---|---|
| 2 | −19.45 | −1.59 | −17.86 |
| 3 | −25.86 | −1.59 | −24.27 |
| 4 | −21.16 | −1.40 | −19.76 |
| 5 | −16.75 | 0.26 | −17.01 |
| 6 | −8.16 | 0.38 | −8.54 |

TABLE 4

IOP lowering effect of *Withania somnifera* and *Areca catechu* with HPMC (F4) in normotensive model

| Time in hours | % Change in IOP Treated eye | % Change in IOP Control eye | % Difference in IOP Treated Eye – Control Eye |
|---|---|---|---|
| 0 | 0 | 0 | 0 |
| 1 | −14.7462 | −2.22854 | −12.5177 |
| 2 | −23.1291 | −1.24795 | −21.8811 |
| 3 | −31.0132 | −2.96783 | −28.0453 |
| 4 | −28.0258 | −1.44005 | −26.5858 |
| 5 | −20.91 | 1.070348 | −21.9804 |
| 6 | −14.7304 | −0.27798 | −14.4524 |
| 7 | −6.09508 | −1.39676 | −4.69832 |

TABLE 5

Comparative data of IOP lowering effect of *Withania somnifera* (F1) and *Areca catechu* (F2) alone and in combination without (F3) or with HPMC (F4) in normotensive model.

| Time (Hours) | % Difference between test and control eye (*W. somnifera*) F1 formulation | % Difference between test and control eye (*A. catechu*) F2 formulation | % Difference between test and control eye (Combination) without HPMC (F3 formulation) | % Difference between test and control eye (Combination) with HPMC (F4 formulation) |
|---|---|---|---|---|
| 0 | 0 | 0 | 0 | 0 |
| 1 | −12.61 | −16.47 | −12.30 | −12.5177 |
| 2 | −17.47 | −19.85 | −17.86 | −21.8811 |
| 3 | −15.54 | −14.95 | −24.27 | −28.0453 |
| 4 | −12.47 | −14.48 | −19.76 | −26.5858 |
| 5 | −8.12 | −9.41 | −17.01 | −21.9804 |
| 6 | −2.85 | −2.58 | −8.54 | −14.4524 |

The result for lowering of IOP by a composition F1 is provided in Table 1, F2 in table 2, F3 in table 3 and F4 in Table 4. It can be seen from all the tables that the IOP is not lowered by the control hence the effect is only due to the composition. It can be seen that the IOP is lowered by all of the compositions, F1 to F4 (Table 1 to 4). However, the % change of IOP in treated eye and % Difference in IOP of Treated Eye-Control Eye is the greatest in the composition containing HPMC, *Withania somifera* and *Areca catechu* (F4) than any other composition (Table 5), suggesting that the composition containing HPMC, *Withania somifera* and *Areca catechu* shows enhanced efficacy to the other compositions. It also indicates that the composition as prepared in Example 1 acts synergistically, in comparison to the composition without HPMC, or without *Withania somifera* or without *Areca catechu*.

EXAMPLE 2

Effect of Composition on Antiglaucoma Activity in Water Loading Model for Glaucoma The composition of Example 1 was prepared (F4) and compared with the composition prepared with the extract of *Withania somnifera* and HPMC but without the extract of *Areca catechu* (F1), another with the extract of *Areca catechu* and HPMC but without the extract of *Withania somifera* (F2). The anti glaucoma activity was evaluated by examining the IOP in rabbits using the water loading model of glaucoma Twelve Albino rabbits of either sex were fasted overnight. Preliminary experiments were conducted to determine the time of administration of drug prior to water load required for appearance of maximal inhibitory effect. One eye was treated with test solution and the contralateral eye serving as control. Ocular hypertension was induced in conscious rabbits by delivering 70 ml/kg body weight by orogastric intubation. IOP was measured every 15-min for a period of 120 minutes.

TABLE 6

IOP lowering effect of *Withania somnifera* with HPMC (F1) in water loaded model

| Time in minutes | % Change in IOP Treated eye | % Change in IOP Control eye | % Difference in IOP Treated Eye – Control eye |
|---|---|---|---|
| 0 | 0.00 | 0.00 | 0 |
| 15 | 17.82 | 42.56 | −24.74 |
| 30 | 46.96 | 77.53 | −30.57 |
| 45 | 48.43 | 87.14 | −38.71 |
| 60 | 40.66 | 72.83 | −32.17 |
| 75 | 36.27 | 65.65 | −29.38 |
| 90 | 32.72 | 58.98 | −26.26 |
| 120 | 10.46 | 17.81 | −7.35 |

TABLE 7

IOP lowering effect of *Areca catechu* with HPMC (F2) in water loaded model

| Time in minutes | % Change in IOP Treated eye | % Change in IOP Control eye | % Difference in IOP Treated Eye – Control eye |
|---|---|---|---|
| 0 | 0.00 | 0.00 | 0.00 |
| 15 | 24.10 | 46.22 | −22.13 |
| 30 | 41.48 | 72.98 | −31.50 |
| 45 | 69.10 | 101.96 | −32.87 |
| 60 | 57.97 | 84.18 | −26.21 |
| 75 | 42.14 | 64.31 | −22.17 |
| 90 | 35.27 | 49.39 | −14.12 |
| 120 | 12.44 | 15.69 | −3.25 |

TABLE 8

IOP lowering effect of Withania somnifera and *Areca catechu* with HPMC (F4) in water loading model

| Time in minutes | % Change in IOP Treated eye | % Change in IOP Control eye | % Difference in IOP Treated Eye – Control Eye |
|---|---|---|---|
| 0 | 0.00 | 0.00 | 0.00 |
| 15 | 25.56 | 50.10 | −24.54 |
| 30 | 45.72 | 79.241 | −33.51 |
| 45 | 64.64 | 111.11 | −46.47 |
| 60 | 76.65 | 118.25 | −41.60 |
| 75 | 67.97 | 100.46 | −32.48 |
| 90 | 43.32 | 66.94 | −23.62 |
| 120 | 13.39 | 18.69 | −5.496 |

TABLE 9

Comparative data of IOP lowering effect of *Withania somnifera* (F1) and *Areca catechu* (F2) alone and in combination with HPMC (F4) in water loading model.

| Time in minutes | % Difference between test and control eye (*W. somnifera*) F1 formulation | % Difference between test and control eye (*A. catechu*) F2 formulation | % Difference between test and control eye (Combination) F4 formulation |
|---|---|---|---|
| 0 | 0 | 0.00 | 0.00 |
| 15 | −24.74 | −22.13 | −24.54 |
| 30 | −30.57 | −31.50 | −33.51 |
| 45 | −38.71 | −32.87 | −46.47 |
| 60 | −32.17 | −26.21 | −41.60 |
| 75 | −29.38 | −22.17 | −32.48 |
| 90 | −26.26 | −14.12 | −23.62 |
| 120 | −7.35 | −3.25 | −5.496 |

The result for lowering of IOP by a composition F1 is provided in Table 6, F2 in Table 7, and F4 in Table 8. It can be seen from all the tables that the IOP is not lowered by the control hence the effect is only due to the composition. It can be seen that the IOP is lowered by all of the compositions, F1, F2 and F4 (Table 6 to 8). However, the % change of IOP in treated eye and % Difference in IOP of Treated Eye-Control Eye is the greatest in the composition containing HPMC, *Withania somifera* and *Areca catechu* (F4) than any other composition (Table 9), suggesting that the composition containing HPMC, *Withania somifera* and *Areca catechu* shows enhanced efficacy to the other compositions. It also indicates that the composition as prepared in Example 1 acts synergistically, in comparison to the composition without *Withania somifera* or without *Areca catechu*.

EXAMPLE 3

Effect of Composition on Antiglaucoma Activity in Steroid Induced Model for Glaucoma The composition of Example 1 was prepared (F4) and compared with the composition prepared with the extract of *Withania somnifera* and HPMC but without the extract of *Areca catechu* (F1), another with the extract of *Areca catechu* and HPMC but without the extract of *Withania somifera* (F2). The anti glaucoma activity was evaluated by examining the IOP in rabbits using the steroid model of glaucoma Young rabbits (twelve) were trained to accept tonometry and then IOP was measured daily for 15 days so as to make a record of baseline IOP. These rabbits were then instilled with prednisolone 1% eye drops (10 μl) in the test eye and normal saline (10 μl) in the control eye, twice a day for a period of 40 days. IOP was measured twice a week during steroid treatment period. At the end of 40 days rabbits were subjected to evaluation of antiglaucoma activity. The concentration of drug showing best effect in normotensive model was further tested in steroid induced glaucoma model. IOP measurements were done at different time intervals. This model mimics the chronic open angle glaucoma.

TABLE 10

IOP lowering effect of *Withania somnifera* with HPMC (F1) in steroid model

| Time in hours | % Change in IOP Treated eye | % Change in IOP Control eye | % Difference in IOP Treated Eye – Control Eye |
|---|---|---|---|
| 0 | 0.00 | 0.00 | 0 |
| 0.5 | −14.16 | −3.03 | −11.13 |
| 1 | −22.32 | −2.75 | −19.57 |
| 1.5 | −25.77 | −3.35 | −22.42 |
| 2 | −29.02 | −1.72 | −27.32 |
| 2.5 | −32.59 | −1.01 | −31.58 |
| 3 | −28.49 | −1.00 | −27.49 |
| 3.5 | −23.15 | −0.67 | −22.48 |
| 4 | −12.29 | 0.38 | −12.67 |
| 5 | −7.14 | −0.31 | −6.83 |
| 6 | −4.02 | 0.04 | −4.06 |

TABLE 11

IOP lowering effect of *Areca catechu* with HPMC (F2) in steroid model

| Time in hours | % Change in IOP Treated eye | % Change in IOP Control eye | % Difference in IOP Treated Eye – Control Eye |
|---|---|---|---|
| 0 | 0.00 | 0.00 | 0.00 |
| 0.5 | −10.92 | −0.92 | −10.00 |
| 1 | −16.18 | −0.52 | −15.66 |
| 1.5 | −19.19 | −1.31 | −17.87 |
| 2 | −25.77 | −2.36 | −23.41 |
| 3 | −22.15 | −2.76 | −19.40 |
| 4 | −16.97 | −1.92 | −15.04 |
| 5 | −12.86 | −2.45 | −10.41 |
| 6 | −5.84 | −2.34 | −3.50 |

TABLE 12

IOP lowering effect of *Withania somnifera* and *Areca catechu*
with HPMC (F4) in steroid model

| Time in hours | % Change in IOP Treated eye | % Change in IOP Control eye | % Difference in IOP Treated Eye − Control Eye |
|---|---|---|---|
| 0 | 0.00 | 0.00 | 0 |
| 1 | −21.87 | −0.336 | −21.534 |
| 2 | −32.19 | −0.805 | −31.385 |
| 3 | −38.03 | −0.666 | −37.364 |
| 4 | −37.29 | −1.843 | −35.447 |
| 5 | −29.76 | −2.055 | −27.705 |
| 6 | −18.80 | −0.688 | −18.112 |
| 7 | −8.56 | −2.055 | −6.505 |

TABLE 13

Comparative data of IOP lowering effect *Withania somnifera*
(F1) and *Areca catechu* (F2) alone and in combination with
HPMC (F4) in steroid model

| Time (Hours) | % Difference between test & control eye (*W. somnifera*) F1 formulation | % Difference between test and control eye (*A. catechu*) F2 formulation | % Difference between test and control eye (Combination) F4 formulation |
|---|---|---|---|
| 0 | 0.00 | 0.00 | 0.00 |
| 1 | −19.57 | −15.66 | −21.534 |
| 2 | −27.32 | −23.41 | −31.385 |
| 3 | −27.49 | −19.40 | −37.364 |
| 4 | −12.67 | −15.04 | −35.447 |
| 5 | −6.83 | −10.41 | −27.705 |
| 6 | −4.06 | −3.50 | −18.112 |

The result for lowering of IOP by a composition F1 is provided in Table 10, F2 in Table 11, and F4 in Table 12. It can be seen from all the tables that the IOP is not lowered by the control hence the effect is only due to the composition. It can be seen that the IOP is lowered by all of the compositions, F1, F2 and F4 (Table 10 to 12). However, the % change of IOP in treated eye and % Difference in IOP of Treated Eye-Control Eye is the greatest in the composition containing HPMC, *Withania somifera* and *Areca catechu* (F4) than any other composition (Table 13), suggesting that the composition containing HPMC, *Withania somifera* and *Areca catechu* shows enhanced efficacy to the other compositions. It also indicates that the composition as prepared in Example 1 acts synergistically, in comparison to the composition without *Withania somifera* or without *Areca catechu*

I claim:

1. An ophthalmic herbal synergistic composition for lowering intraocular pressure in the eye of a patient, wherein the active ingredient in the composition consists essentially of an extract of *Withania Somnifera* in an amount of from 0.01 to 5.0% w/v, an extract of *Areca catechu* in an amount of from 0.01 to 5.0% w/v, and hydroxy propyl methyl cellulose in an amount of from 0.1 to 2% w/v.

2. The composition of claim 1, wherein viscosity of the composition is in the range of 10-100 cps.

3. The composition of claim 1, wherein osmolality of the composition is in the range of 250-450 mOsm.

4. The composition of claim 1, wherein pH of the composition is in the range of 4-8.

5. The composition of claim 1, wherein the composition is packed in a container that is colored, opaque, plastic or glass.

6. The composition of claim 1, wherein the composition is in a form selected from the group consisting of eye drops, ointment, cream, and gel.

* * * * *

UNITED STATES PATENT AND TRADEMARK OFFICE
CERTIFICATE OF CORRECTION

PATENT NO.       : 8,178,134 B2
APPLICATION NO.  : 12/216041
DATED            : May 15, 2012
INVENTOR(S)      : Suresh Kumar Gupta It is certified that error appears in the above-identified patent and that said Letters Patent is hereby corrected as shown below:

<u>Title page,</u>
Item (73), Assignee, change "Delhi Institute of Pharmaceuticals and Research", to --Delhi Institute of Pharmaceutical Sciences and Research--

Signed and Sealed this
Twenty-second Day of January, 2013

David J. Kappos
*Director of the United States Patent and Trademark Office*